United States Patent [19]

Sommer

[11] Patent Number: 4,942,305
[45] Date of Patent: Jul. 17, 1990

[54] INTEGRATING SPHERE AEROSOL PARTICLE DETECTOR

[75] Inventor: Holger T. Sommer, Greenbelt, Md.

[73] Assignee: Pacific Scientific Company, Newport Beach, Calif.

[21] Appl. No.: 350,769

[22] Filed: May 12, 1989

[51] Int. Cl.⁵ ............................................. G01N 15/06
[52] U.S. Cl. ................................. 250/574; 250/228; 356/343; 356/339
[58] Field of Search ........ 250/574, 575, 228, 564–565; 356/338–343, 441, 442, 236

[56] References Cited

U.S. PATENT DOCUMENTS

| | | | |
|---|---|---|---|
| 3,624,835 | 11/1971 | Wyatt | 250/574 |
| 3,826,574 | 7/1974 | Brown, Jr. | 356/236 |
| 3,838,926 | 10/1974 | Kato et al. | 250/228 |
| 3,869,208 | 3/1975 | Lorenz | 250/228 |
| 4,320,978 | 3/1982 | Sato | 250/228 |
| 4,690,560 | 9/1987 | Coogan | 356/236 |
| 4,746,215 | 5/1985 | Gross | 356/339 |

Primary Examiner—David C. Nelms
Assistant Examiner—Khaled Shami
Attorney, Agent, or Firm—Lane, Aitken & McCann

[57] ABSTRACT

An integrating sphere for detecting particles in an aerosol has a diffuse reflectant interior surface and a plurality of photodetectors. The aerosol passing through aligned ducts which are spaced at the center of the integrating sphere, and a beam of collimated light, such as a laser beam, projects transversely through the aerosol in the space. Particles in the aerosol scatter the light, and the scattered light is detected simultaneously by the photodetectors within the integrating sphere. A coincidence detection circuit is used to detect the number of times scattered light is simultaneously detected by the photodetectors and, thereby, count the number of particles in the aerosol.

10 Claims, 3 Drawing Sheets

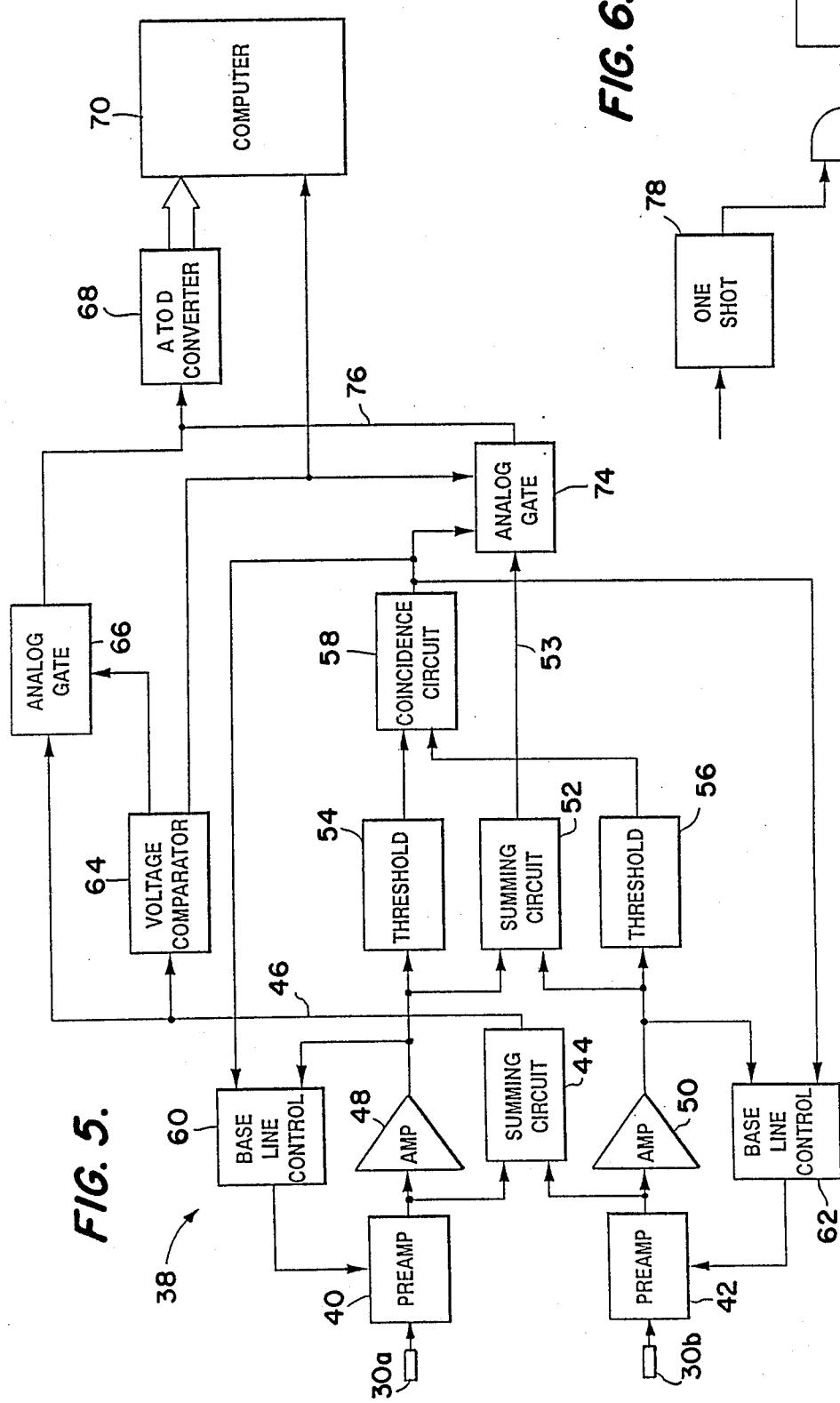
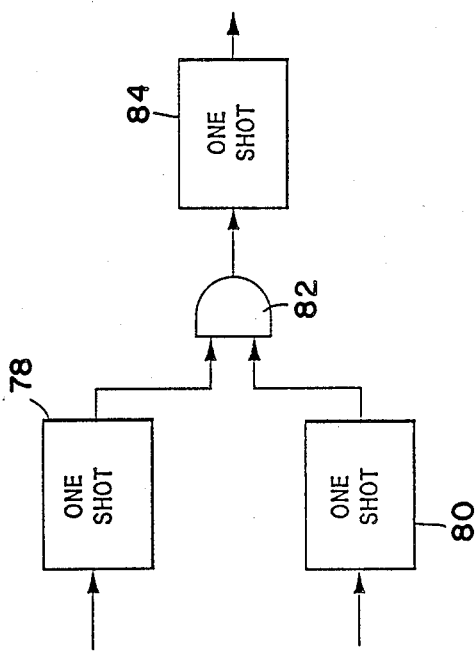

INTEGRATING SPHERE AEROSOL PARTICLE DETECTOR

BACKGROUND OF THE INVENTION

The present invention relates to apparatus for detecting particles in an aerosol by light scattering and, more particularly, to a system employing an integrating sphere for detecting and measuring particles as small as submicron size in aerosols.

Particles in aerosols have been detected by detecting light scattered by the particles as they pass through a beam of light, such as a laser beam. In prior art systems, the scattered light is collected by a lens or lenses and focused on a photodetector. The amplitude of each resulting pulse generated by the photodetector in response to a particle indicates particle size. When an elongate particle scatters light in such a system, light is scattered with different intensities in different directions. As a result, the pulse amplitude will depend upon the particle orientation as it passes through the laser beam. In addition, the lenses of such systems of the prior art are subject to contamination, and, in the manufacture of such a system, the lens or lenses have to be carefully aligned with the photodetector and the locus in which the particle encounters the laser beam.

An integrating sphere has been used in connection with a laser beam in a turbidimeter to measure the turbidity of a sample liquid by optical diffusion where the sample liquid contains dispersed particles of submicron size in an extremely low concentration. The liquid sample is guided through the interior of the integrating sphere by a cylindrical sample cell, and a collimated beam of light is projected axially through the cell and the sample therein.

SUMMARY OF THE INVENTION

By the present invention, particles in an aerosol sample, are detected through the use of an integrating sphere.

The aerosol sample is fed in a gas stream through the integrating sphere, being formed into a thin, flat laminar flow jet, open to the interior of the integrating sphere through which a laser beam is transversely projected. The interior surface of the integrating sphere is covered with a highly efficient diffuse reflectant material, and a plurality of photodetectors are mounted at spaced positions on the integrating sphere. Light from the laser beam scattered by particles in the aerosol sample is multiply reflected by the diffuse reflectant material on the inside surface of the integrating sphere, which integrates the scattered light over the interior surface of the sphere. The photodetectors detect the integrated scattered light multiply reflected from the interior surface of the integrating sphere, and coincidence signal processing is used to distinguish actual light scattering from noise associated with the photodetectors and light source.

When the elongate or unevenly shaped particles pass through the laser beam, the different intensities of light scattered in different directions will be integrated into a uniform intensity over the interior surface of the sphere and the integrated light with this uniform intensity will be applied to each photodetector. As a result, each photodetector will generate a pulse amplitude which is dependent essentially only on the size of the particle and which is substantially independent of the particle shape or particle orientation in the laser beam. In addition, the integrating sphere by diffusely and multiply reflecting the scattered light around the interior surface of the sphere increases the intensity of the light received by each photodetector to a multiple of the light received by a photodetector employing optics to collect the scattered light and focus it on a photodetector. In this manner, the signal to noise ratio of the pulses is increased relative to the prior art particle size measuring systems. Since no lenses or other optics are required, the alignment and contamination problems associated with the prior art systems are eliminated.

In one embodiment of the detector according to the present invention, the laser can be mounted externally to the integrating sphere, and the laser beam is allowed to pass entirely through the integrating sphere and is trapped at the side of the integrating sphere remote from the laser. In another embodiment, a mirror is mounted on the interior of the sphere at a point opposite the laser to define an external laser cavity. Thus, the aerosol sample passes through and the light scattering by the particles occurs in the external cavity of the laser.

BRIEF DESCRIPTION OF THE DRAWINGS

FIG. 5 is a block diagram illustrating the circuitry used with the integrating sphere particle detector of FIGS. 1 and 2; and FIG. 6 is a block diagram illustrating the coincidence circuitry employed in the system of the present invention.

DETAILED DESCRIPTION OF THE PREFERRED EMBODIMENTS

Figure 1:
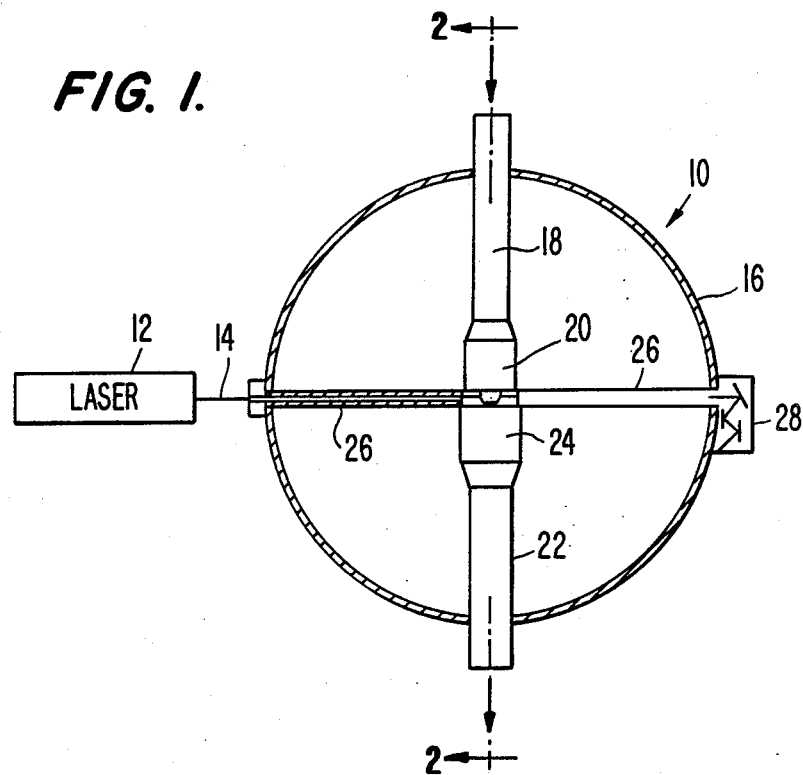
FIG. 1 is a schematic cross section of one embodiment of the integrating sphere aerosol particle detector according to the present invention.

As can be seen from FIG. 1, the integrating sphere aerosol detector according to the present invention, which is designated generally by the reference numeral 10, includes a laser 12, such as a He-Ne laser, projecting a laser beam 14 through an integrating sphere 16. The interior surface of the integrating sphere is covered with a highly efficient diffuse reflectant material, such as material having a matte surface, as is known in the art of integrating spheres, and the integrating sphere has a diameter typically on the order of 2 or 3 inches.

An aerosol sample is guided in a gas stream through the integrating sphere 16 in a direction transverse to the laser beam 14 by an inlet duct 18 having a nozzle 20, the inlet duct extending from the integrating sphere 16 to a point just short of the center of the integrating sphere. An outlet duct 22 having a flared inlet 24, spaced slightly from the nozzle 20 extends from a point just short of the center of the integrating sphere 16 to the integrating sphere. The laser beam 14 passes through the integrating sphere 16 within tubular covers 26 which are spaced from one another at the center of the integrating sphere 16, where the laser beam 14 intersects the stream of the aerosol sample. The tubular covers 26 shield the laser beam 14, preventing it from radiating light around the integrating sphere 16. In the embodiment illustrated in FIGS. 1 and 2, the laser beam 14 passes out the side of the integrating sphere 16 remote from the laser 12 where it may be stopped by a laser beam trap 28. The nozzle 20 of the inlet tube 18 terminates near the center of the integrating sphere 16, slightly short of the line along which the laser beam 14 travels. The nozzle 20 forms the sample stream into a thin, flat laminar jet flow narrower than the laser beam 12, which assures that all of the sample passes through the laser beam 12, thereby resulting in accurate detection and measurement of the particles in the sample stream. The flared inlet 24 of the outlet duct 22 is shaped to take in all of the sample stream passing out of the nozzle 20 and to guide it into the outlet duct 22 for passage out of the integrating sphere 16. A device (not shown), for example, a vacuum pump connected to the outlet duct 22, is provided for moving the sample stream through the integrating sphere 16 at a flow rate on the order of, for example, 1 ft.$^3$/min. The nozzle 20 is fully described in U.S. Pat. No. 4,746,215, in the name of Kenneth P. Gross, which is assigned to the assignee of the present invention.

Figure 2:
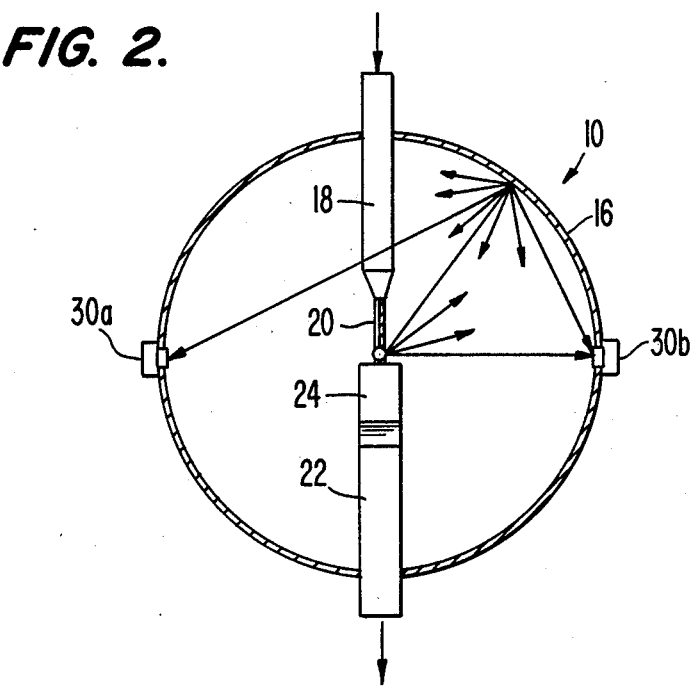
FIG. 2 is a schematic cross section taken along the line 2—2 of FIG. 1.

A plurality of photodetectors 30a and 30b comprising photocells are mounted at spaced positions on the integrating sphere 16 with their light-sensitive elements exposed to the interior of the integrating sphere. Although only two photodetectors 30a and 30b are illustrated in FIG. 2, a greater number can be used, as can be seen from FIG. 4. When only two photodetectors are used, they are ordinarily positioned at opposite ends of an axis.

In operation, when the laser beam 14 projects through the integrating sphere 16, and the sample stream passes through the laser beam 14 at the center of the integrating sphere 16, the small particles scatter the light of the laser beam 14 as they pass through it. A small amount of the scattered light will impinge directly on the photodetectors 30a and 30b. However, most of the scattered light impinges upon the interior surface of the integrating sphere 6 and is multiply reflected. This interior surface is covered with a highly efficient diffuse reflectant material, such as a matte surface, which diffusely reflects the scattered light, and integrates the scattered light over the interior surface of the sphere. As a result, any directional differences in intensity in the light scattered by a particle will be averaged out by the integration and each photodetector will generate an output pulse having an amplitude corresponding to the size of the particle substantially independently of the particle shape and orientation of the particle as it passes through the laser beam. Coincidence signal processing is used to detect the number of times light strikes both detectors 30a and 30b simultaneously and, thereby, count the particles which scatter the light, as will be described in greater detail hereinafter.

Figure 3:
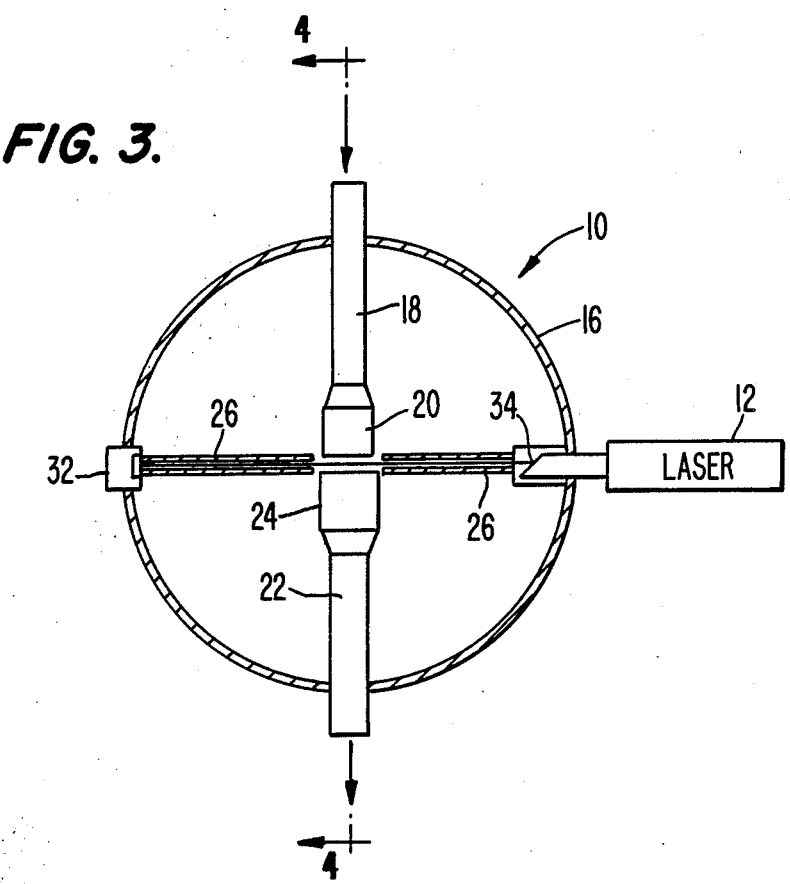
FIG. 3 is a schematic cross section of an alternate embodiment of the integrating sphere particle detector according to the present invention.
Figure 4:
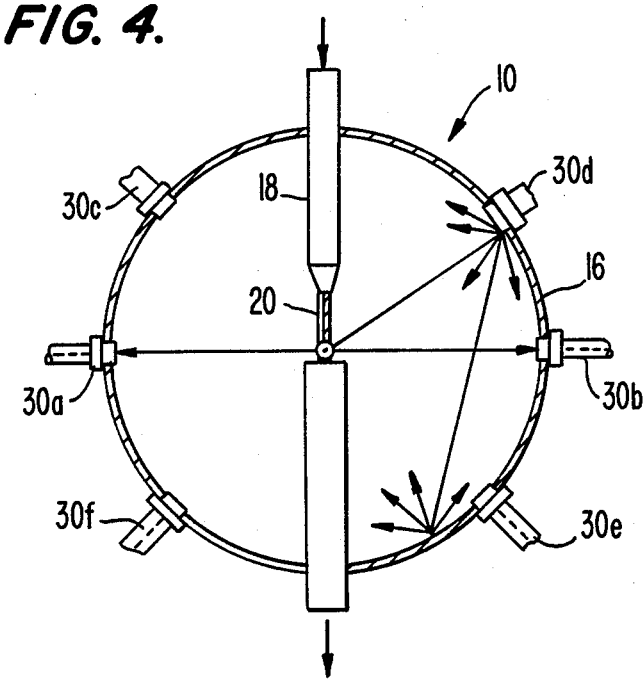
FIG. 4 is a schematic cross section taken along the line 4—4 in FIG. 3.

Another embodiment of the present invention can be seen from FIGS. 3 and 4. This embodiment is similar to the embodiment of FIGS. 1 and 2, but the laser light does not pass out through the side of the integrating sphere 16. Instead, a mirror 32, such as a spherical mirror, is mounted on the interior surface of the integrating sphere 16 at a point opposite the laser 12 to reflect light back into the laser. In addition, the laser light enters the integrating sphere 16 through a Brewster window 34. In this embodiment, a half-silvered mirror which would ordinarily be positioned at the outlet end of the laser 12 is omitted, and an external laser cavity is defined in the integrating sphere 16. The angles of the Brewster window 34 are chosen to minimize the reflection of light and, thereby, minimize losses when the light passes through the Brewster window. Although the Brewster window 34 is illustrated inside the integrating sphere 16, it could also be positioned outside the integrating sphere. Airtight seals are provided around every element, such as the inlet duct 18, the outlet duct 22, and the photodetectors 30a - 30f, which project through the wall of the integrating sphere 16. Although six photodetectors are shown in FIG. 4, other numbers of photodetectors can also be used in this embodiment, including two photodetectors, as are used in the embodiment shown in FIGS. 1 and 2.

The coincidence signal processing increases the capability of the system according to the present invention to distinguish pulses caused by small particles from noise by providing the integrating sphere 16 with at least two photodetectors to detect light scattered from the light beam 14 by using a coincidence circuit to determine when two photodetectors simultaneously generate pulses indicating the presence of a small particle. If both photodetectors generate a pulse simultaneously, then there is a high probability that the pulses were caused by a particle and were not simultaneous noise variations in the output signals from the photodetectors. The ability of the system to distinguish low amplitude pulses caused by particles from noise enables the system to detect the presence of small particles better than the systems of the prior art.

FIG. 5 is a block diagram of a coincidence circuit 38 to determine when two photodetectors generate a pulse simultaneously. Any particle in the sample stream will pass through the laser beam and scatter light directly to the diffuse reflectant material on the inner surface of the integrating sphere 16. The diffuse reflectant material causes the light to be multiply reflected to integrate the scattered light, which is then detected by the photodetectors, for example, photodetectors 30a and 30b.

When two photodetectors 30a and 30b are used, as in FIGS. 1 and 2, the output signals of the photodetectors 30a and 30b are amplified by preamplifiers 40 and 42 and then are applied to a summing circuit 44 in which the two signals are added together to produce a low gain analog signal on a channel 46. The output signals from the preamplifiers 40 and 42 are also amplified by amplifiers 48 and 50 and then added together by a summing circuit 52 to produce a high gain analog signal on a channel 53. The output signals from the amplifiers 48 and 50 are also applied to threshold circuits 54 and 56, each of which generates a high level constant amplitude output signal whenever the applied input signal rises above a predetermined threshold. As a result, each of the threshold circuits 54 and 56 will produce a train of square wave pulses in response to the output pulses from the amplifiers 48 and 50 caused by particles passing through the laser beam 14 in the integrating sphere 16. A coincidence circuit 58 detects whenever there is a coincidence in the rise times of the square wave pulses applied from the threshold detectors 54 and 56, and, whenever such a coincidence occurs, the coincidence circuit 58 generates an output pulse indicating that a particle is passing through the laser beam. The output pulses of the coincidence circuit 58 have a pulse length corresponding to the length of the pulses generated by the photodetectors 30a and 30b in response to particles and are applied to base line control circuits 60 and 62, which also receive the output signals from the amplifiers 48 and 50, respectively. The base line control circuits 60 and 62 integrate the output signals from the amplifiers 48 and 50 except when receiving a pulse from the coincidence circuit 58 indicating that a particle is present. The base line control circuits apply the integrated output signals as base line input signals to the preamplifiers 40 and 42, which produce amplified outputs corresponding to the differences between the signals applied from the baseline control circuits 60 and 62 and the signals received from the photodetectors 30a and 30b. In this manner, the baselines of the preamplifiers 40 and 42 are controlled in accordance with the average of output of the photodetectors 30a and 30b except when the photodetectors 30a and 30b are receiving scattered light from a particle.

The output signal from the summing circuit 44 on channel 53 is applied to a voltage comparator 64 and to an analog gate 66. When the output signal from the summing circuit 44 is above a predetermined amplitude, the voltage comparator 64 will enable the analog gate to pass the output signal from the summing circuit 44 to an analog to digital converter 68. Thus, when a pulse in the output of the summing circuit 44 is large enough to cause the voltage comparator 64 to enable the analog gate 66, this output pulse will be passed to the analog to digital converter 68. The analog to digital converter 68 is of the type which converts the peak amplitude of the applied input pulse to a digital value and applies the resulting digital value to a computer 70, which registers and responds to each received digital value in the manner described in copending application Ser. No. 144,225, filed Jan. 15, 1988 by Kenneth Von Bargen.

If the output signal from the summing circuit 44 is below the threshold value for the voltage comparator 64, the voltage comparator 64 will apply an enabling signal to an analog gate 74, which also receives the output pulses produced by the coincidence circuit 58. The analog gate 74 is enabled by receiving simultaneously a pulse from the coincidence circuit 58 and an enabling signal from the voltage comparator 64. When the gate 74 is enabled, a pulse will be present on a high gain signal channel 76 caused by a small particle. The gate 74, when enabled, will pass the pulse on the channel 76 to the analog to digital converter 68 which will convert the peak amplitude of the pulse to a digital value and apply the digital value to the computer 70. The voltage comparator 64 also applies a signal to the computer 70 to indicate to the computer whether the digital value came through the analog gate 66 or the analog gate 74 so that the computer can properly scale the received digital signal.

As described in a copending application, Ser. No. 07/144,225, filed on Jan. 15, 1988, the computer 70 is programmed to increment a count in its memory corresponding to the received digital value so that a count of particle sizes in each individual size range represented by a different digital value received from the analog-to-digital converter 55 is obtained. The computer 57 is also operable to display the counts of the different particle size ranges.

FIG. 6 is a block diagram illustrating the details of the coincidence circuit 58. As shown in FIG. 6, the output pulses from the threshold detectors 54 and 56 are applied to one shot multivibrators 78 and 80, which are connected to be triggered in response to the leading edges of received pulses from the threshold detectors. The outputs from the one shot multivibrators are applied to an AND gate 82, which accordingly will produce an output pulse whenever one of the shot multivibrators 78 and 80 is triggered to produce an output pulse at a time when the other one shot multivibrator has been triggered and still remains in its triggered state. Thus, the gate 82 will produce an output pulse when the rise time of the two output pulses from the threshold circuits 54 and 56 occur within a predetermined time interval of one another determined by the timing of the one shot multivibrators 78 and 80. This time interval is set to be a small fraction of the pulse length of the pulses generated by particles passing through the integrating sphere 16. Any output pulse produced by the gate 82 triggers a one shot multivibrator 84, which in response to being triggered produces an output pulse length corresponding to the approximate pulse lengths of the pulses generated by the photodetectors 30a and 30b caused by particles. The output pulse from the one shot multivibrator 84 is the enabling signal applied from the coincidence circuit 58 to the analog gate 74 and to the base line control circuits 60 and 62 as shown in FIG. 5.

When more than two photodetectors are used, as in FIGS. 3 and 4, only two photodetectors are used for coincidence detection. The signals from the other photodetectors are summed, after preamplification, with the signals from the photodetectors used for coincidence detection in order to further improve the signal to noise ratio.

A number of modifications of and additions to the specific embodiments of the invention described above may be made without departing from the spirit and scope of the invention, which is defined in the appended claims. For example, instead of a He-Ne laser, a diode laser could be used. In that case, a Brewster window would not be used. Other sources of collimated light beams can be used and lasers can be omitted altogether, although lasers are presently the most efficient sources of collimated light.

I claim:

1. Apparatus for detecting particles in a gas stream comprising:
   an integrating sphere having an interior surface;
   means for conducing the gas stream through said integrating sphere;
   means for projecting a collimated light beam transversely through said gas stream in said integrating sphere, whereby the particles in the gas stream scatter light from said light beam;
   means for detecting light scattered from said light beam within said integrating sphere, said light detecting means comprising a plurality of photodetectors mounted on said integrating sphere,
   and coincidence detection means for detecting the simultaneous light detection by at least two of said photodetectors.

2. The apparatus according to claim 1, wherein said means for conducting the gas stream comprises an inlet duct extending from said integrating sphere to a first point just short of the center of the integrating sphere and an outlet duct axially aligned with said inlet duct and extending from a second point just short of the center of said integrating sphere to said integrating sphere.

3. The apparatus according to claim 2, wherein said inlet duct includes a flat nozzle forming the gas stream into a thin, flat shape, and said outlet duct includes a flared inlet to take in all of the thin, flat gas stream issuing from the nozzle.

4. The apparatus according to claim 2, wherein said light beam traverses said gas stream between said first and second points.

5. The apparatus according to claim 1, wherein said light beam projecting means comprises a laser.

6. The apparatus according to claim 5, wherein said light beam enters said integrating sphere on one side of said integrating sphere and projects to an opposite side of said integrating sphere.

7. The apparatus according to claim 6, wherein a beam trap is positioned at said opposite side of said integrating sphere.

8. The apparatus according to claim 6, wherein said laser includes a Brewster window, said light beam projects from said laser through said Brewster window, and means for reflecting said light beam back through said Brewster window is positioned at said opposite side of said integrating sphere.

9. The apparatus according to claim 1, further comprising means for measuring the intensity of the scattered light detected by said light detecting means.

10. An apparatus for detecting particles in a gas stream comprising:
   an integrating sphere having an interior surface,
   means for conducting a gas stream through said integrating sphere;
   a laser for directing a laser beam across said integrating sphere through said gas stream in said integrating sphere, said laser having a brewster window at one end thereof positioned on one side of said integrating sphere and a mirror on the opposite side of said integrating sphere positioned to reflect the laser beam back through said brewster window into said laser, said brewster window and said mirror defining an external cavity for said laser, and means for detecting light scattered by particles in said gas stream from said laser beam within said integrating sphere.

* * * * *